US00PP35769P3

(12) United States Plant Patent
Scheffers

(10) Patent No.: US PP35,769 P3
(45) Date of Patent: Apr. 23, 2024

(54) ***CEROPEGIA* PLANT NAMED 'REMY'**

(50) Latin Name: ***Ceropegia linearis* E. Mey. subsp. *woodii* (Schltr.) H. Huber syn. *Ceropegia woodii***
Varietal Denomination: Remy

(71) Applicant: Aad Scheffers, Honselersdijk (NL)

(72) Inventor: Aad Scheffers, Honselersdijk (NL)

( * ) Notice: Subject to any disclaimer, the term of this patent is extended or adjusted under 35 U.S.C. 154(b) by 0 days.

(21) Appl. No.: 17/803,883

(22) Filed: Jan. 9, 2023

(65) Prior Publication Data

US 2023/0403958 P1 Dec. 14, 2023

(30) Foreign Application Priority Data

Jun. 13, 2022 (QZ) ..... 2022/1478

(51) Int. Cl.
*A01H 6/08* (2018.01)
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 6/08; A01H 5/12; A01H 5/02
See application file for complete search history.

*Primary Examiner* — Keith O. Robinson
(74) *Attorney, Agent, or Firm* — Samuel R. McCoy, Jr.

(57) ABSTRACT

A new and distinct *Ceropegia woodii* plant named 'Remy' which is characterized by a trailing habit, small narrowly cordate to near-deltoid foliage, non-variegated foliage, a fast rate of growth, as well as the stability of these characteristics from generation to generation.

2 Drawing Sheets

Latin name of the genus and species: The Latin name of the genus and species of the novel variety disclosed herein is *Ceropegia linearis* E. Mey. subsp. *woodii* (Schltr.) H. Huber syn. *Ceropegia woodi.*

Variety denomination:

The inventive variety of *Ceropegia* disclosed herein has been given the variety denomination 'Remy'.

CROSS REFERENCE TO RELATED APPLICATIONS

This application claims priority to the Community Plant Variety Rights application number 2022/1478, filed Jun. 13, 2022, which is herein incorporated by reference.

BACKGROUND OF THE INVENTION

Parentage: The new plant originated as a spontaneous, partial-plant, branch mutation. The branch mutation was discovered at a greenhouse in Honselersdijk, The Netherlands, in March of 2020, growing amongst a plurality of cultivated *Ceropegia woodii* 'Green Love' (not patented) plants. The mutation exhibited non-variegated foliage and improved vigor, relative to the parent. From said mutated branch, twelve vegetative cuttings were harvested, rooted, and grown to a mature size in order to evaluate stability and uniqueness of the characteristics first observed. Of these twelve plants, most exhibited at least some degree of reversion in the foliage color, back to the variegated parental phenotype. Any of plant that showed reversion was discarded while stem cuttings were harvested from those plants that retained solid green foliage. This process was repeated several times until all progeny from an individual cutting retained the characteristics first observed in March of 2020.

Asexual Reproduction: Asexual reproduction of the new cultivar 'Remy', by way of softwood stem cuttings, was first initiated in March of 2020 in Honselersdijk, The Netherlands. Through more than 6 subsequent generations, the unique features of this cultivar have proven to be stable and true to type.

SUMMARY OF THE INVENTION

The cultivar 'Remy' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Remy'. These characteristics in combination distinguish 'Remy' as a new and distinct *Ceropegia* cultivar:

1. *Ceropegia* 'Remy' exhibits relatively small, narrowly cordate to near-deltoid foliage; and
2. *Ceropegia* 'Remy' exhibits green, non-variegated foliage; and
3. *Ceropegia* 'Remy' exhibits a fast growth rate.

BOTANICAL DESCRIPTION OF THE PLANT

Figure 1:
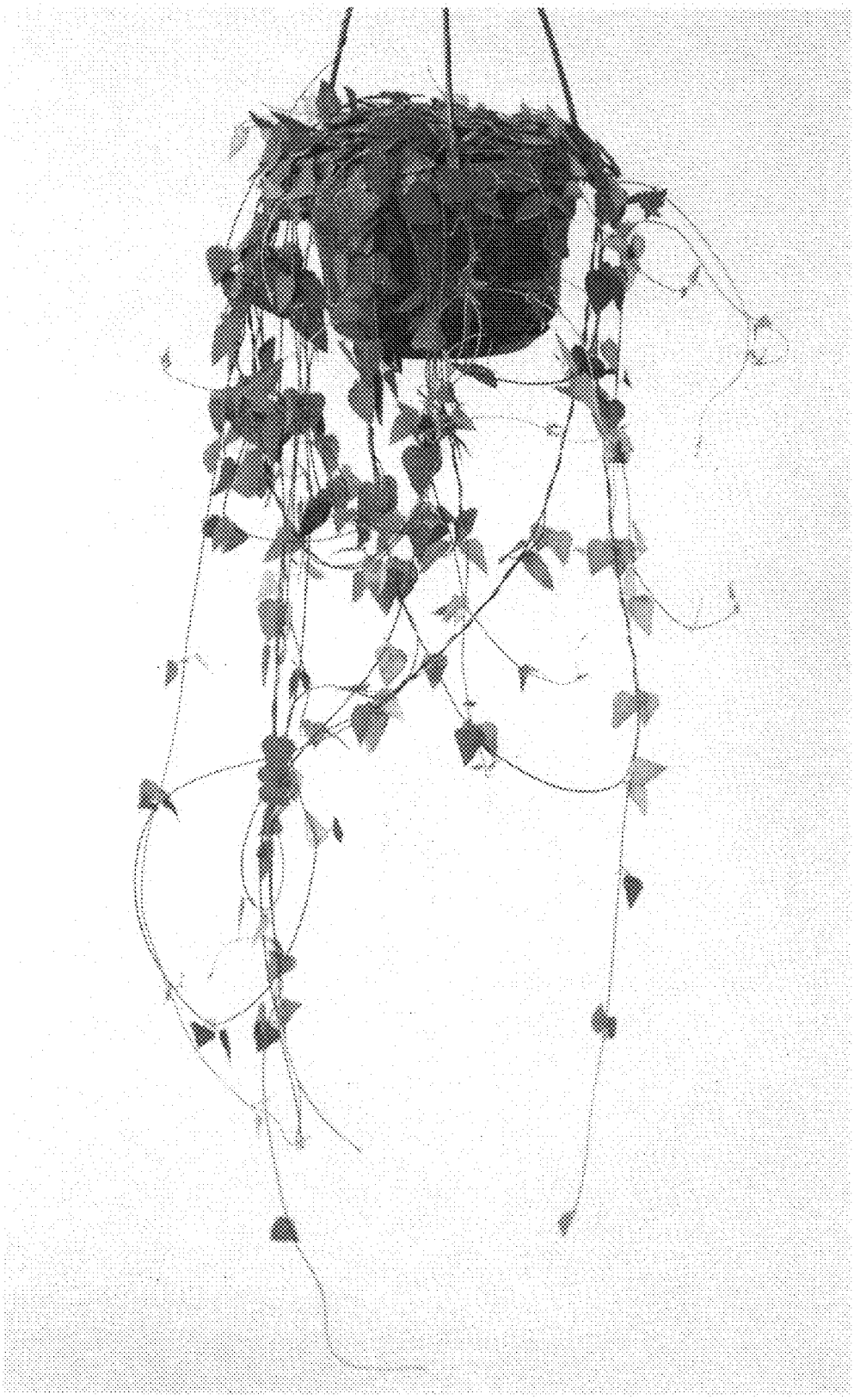
FIG. 1 illustrates, as nearly true as it is reasonably possible to make the same in color photographs of this type, an exemplary 12-month-old 'Remy' plant in a 13 cm nursery pot, grown in a greenhouse in Honselersdijk, The Netherlands.
Figure 2:
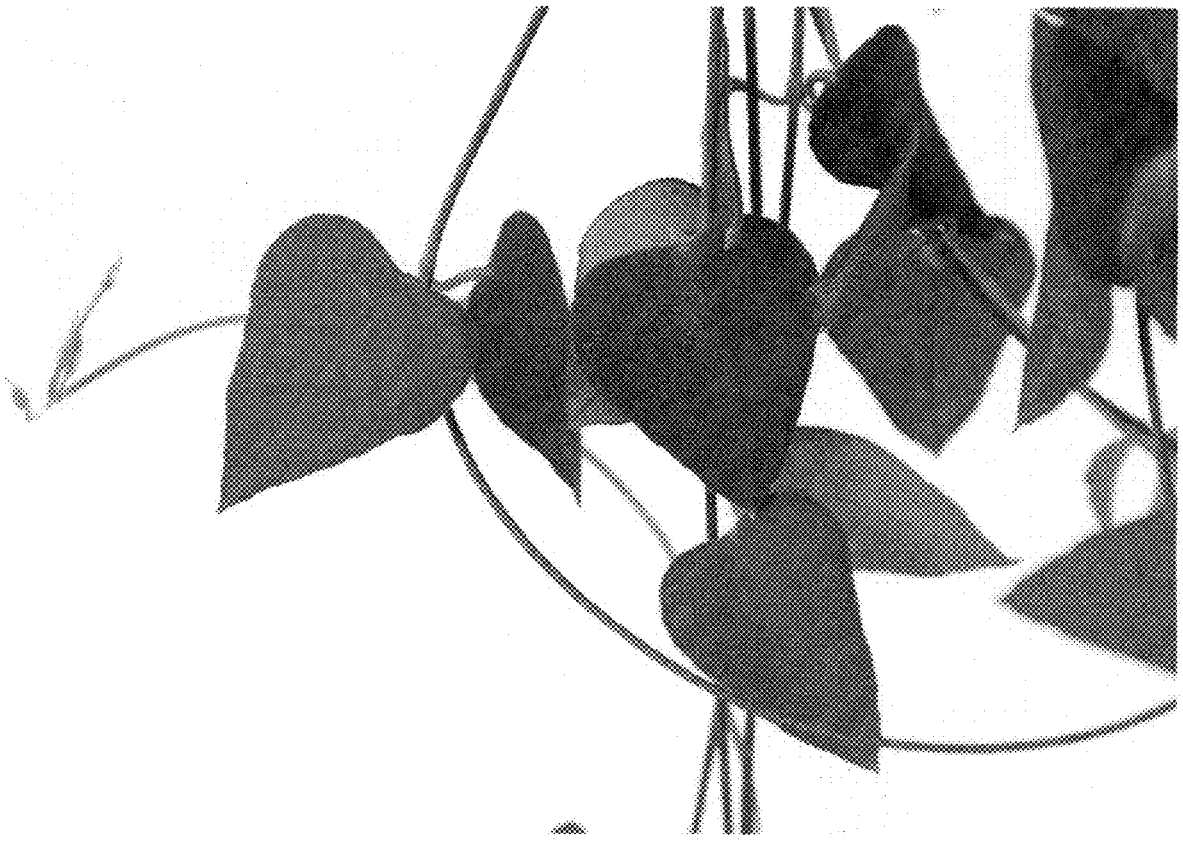
FIG. 2 illustrates, as nearly true as it is reasonably possible to make the same in color photographs of this type, the mature foliage of 'Remy'.

The following observations and measurements were made in August of 2022 and describes a 12-month-old 'Remy' plant grown in a 13 cm nursery pot grown in a greenhouse in Honselersdijk, The Netherlands. Plants were grown using conventional greenhouse production protocols for *Ceropegia* which consisted of growing under 50 percent shade with regular irrigation and fertilizer applications as needed. Pesticides were used to control thrips, but no pest or disease control measures were otherwise utilized in production. No photoperiodic treatments or artificial light was given to the plants.

Those skilled in the art will appreciate that certain characteristics will vary with older or, conversely, with younger plants. 'Remy' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2015 (sixth edition).

A botanical description of 'Remy' and comparisons with the parent and most similar commercial variety of *Ceropegia* are provided below.

Plant description:

*Growth habit.*—Evergreen trailing vine perennial.

*Average height from base to top of foliage.*—In a hanging basket, the plant is 78.0 cm from the top of the floral plane to the apex of the lowest trailing stem.

*Average width.*—29.3 cm.

*Growth rate.*—Moderately fast growing.

*Plant vigor.*—Moderately vigorous.

*Propagation method.*—Softwood stem cuttings; rooting is initiated in approximately 14 days, when grown in a greenhouse with an ambient average temperature of 20 degrees Celsius.

*Time to produce a finished plant.*—Approximately 5 months is required to produce a fully rooted and marketable 11 cm plant when grown under greenhouse conditions.

*Disease and pest resistance or susceptibility.*—Plants have not been observed to be susceptible or resistant to pathogens and pests common to *Ceropegia* sp.

*Environmental tolerances.*—Adapt to at least USDA Zones 8 and 12; moderate tolerance to rain; high tolerance to wind; moderate tolerance to drought.

Root system:

*General.*—Caudices at the base of main stems, at and slightly below the soil level, give rise to a moderately dense network of fleshy roots.

*Distribution in the soil profile.*—Roots are relatively shallow.

*Texture.*—Fleshy; no root hairs present.

Stem:

*Branching habit.*—Basally branching main stem; freely branching with lateral branches.

*Number of main stems per plant.*—15.

*Number of lateral branches per plant.*—10.

*Aspect.*—Rounded.

*Length of main stems.*—63.8 cm.

*Diameter of main stems.*—0.125 cm at the widest point.

*Internode length on main stems.*—7.7 cm.

*Attitude.*—Prostrate; weeping, when grown in a hanging basket.

*Strength.*—Moderately strong.

*Texture and luster.*—Glabrous and matte.

*Color, juvenile.*—Yellow-green, nearest to RHS 144A.

*Color, mature.*—Greyed-green, nearest to RHS 197A yet darker, and finely blotched with yellow-green, nearest to RHS N148A.

*Color at internodes.*—Greyed-green, nearest to RHS 197A, and finely blotched with yellow-green, nearest to RHS N148A.

Foliage:

*Arrangement.*—Opposite.

*Division.*—Simple.

*Attachment.*—Petiolate.

*Quantity.*—Average of 18 leaves per lateral branch.

*Lamina.*—Dimensions — 2.4 cm long and 2.1 cm wide, on average. Shape — Narrow cordate to near deltoid. Aspect — Flat. Apex — Acute. Base — Cordate to shallowly truncate. Margin — Entire; not undulated. Pubescence, texture and luster of adaxial surface — Glabrous, smooth, and very slightly glossy. Pubescence, texture and luster of abaxial surface — Glabrous, smooth, and very slightly glossy. Color — Juvenile foliage, adaxial surface — Green, nearest to RHS 137B. Juvenile foliage, abaxial surface — Green, nearest to RHS 138B. Mature foliage, adaxial surface — Green, nearest to RHS NN137A. Mature foliage, abaxial surface — Greyed-green, nearest to RHS 191B; often but not always suffused with greyed-purple, nearest to RHS 183D. Venation — Pattern — Pinnate. Venation color, adaxial surface — Green, nearest to RHS NN137A. Venation color, abaxial surface — Yellow-green, nearest to RHS 146C; suffused with a mixture of greyed-purple and grey, RHS N187C and 201B.

*Petiole.*—Length — 0.5 cm. Width — 0.1 cm. Texture — Smooth and glabrous. Luster — Matte. Strength — Moderately strong. Color, adaxial surface — Yellow-green, nearest to RHS 148B; lightly suffused with greyed-red, nearest to RHS 182D. Color, abaxial surface — Greyed-orange, nearest to RHS 177D; lightly suffused with greyed-red, nearest to RHS 182D.

Inflorescence: To date, no flowering has been observed.

Bud: To date, no flowering has been observed.

Flower: To date, no flowering has been observed.

Reproductive organs: To date, no flowering has been observed.

Seed and fruit: To date, no flowering has been observed.

Comparisons with the parent plant: Plants of the new cultivar 'Remy' differ from *Ceropegia woodii* 'Green Love' (not patented) parent by the characteristics described in Table 1.

TABLE 1

| Characteristic | 'Remy' | 'Green Love' |
|---|---|---|
| Rate of growth. | Faster-growing than 'Green Love'. | Slower-growing than 'Remy'. |
| Presence of foliage variegation. | Not present; adaxial foliage surface is solid green. | Present; adaxial foliage surface is green with light greyed-green mottling. |

Comparison with the most similar *Ceropegia* cultivar known to the inventor: Plants of the new cultivar 'Remy' differ from the commercial variety, *Ceropegia* 'Variegata' (not patented), in the following characteristics described in Table 2 below.

TABLE 2

| Characteristic | 'Remy' | 'Variegata' |
|---|---|---|
| Rate of growth. | Faster-growing than 'Variegata'. | Slower-growing than 'Remy'. |
| Foliage shape. | Narrow cordate to near deltoid. | Broadly cordate to nearly-round. |
| Foliage size. | Smaller than 'Variegata'. | Larger than 'Remy'. |
| Presence of foliage variegation. | Not present; adaxial foliage surface is solid green. | Present; adaxial foliage surface is green with light greyed-green mottling and broad cream-white margins which are often suffused with red purple. |

That which is claimed is:

1. A new and distinct *Ceropegia woodii* plant named 'Remy', substantially as described and illustrated herein.

* * * * *